United States Patent
Yonemura et al.

(10) Patent No.: US 7,635,577 B2
(45) Date of Patent: Dec. 22, 2009

(54) PROCESS FOR PRODUCING HUMAN THROMBIN BY GENE MODIFICATION TECHNIQUE

(75) Inventors: Hiroshi Yonemura, Kumamoto-ken (JP); Tajayuki Imamura, Kumamoto-ken (JP); Hiroshi Nakatake, Kumamoto-ken (JP); Kenji Soejima, Kumamoto-ken (JP); Chikateru Nozaki, Kumamoto-ken (JP)

(73) Assignee: Juridical Foundation The Chemo-Sero-Therapeutic Research Institute, Kumamoto-ken (JP)

( * ) Notice: Subject to any disclaimer, the term of this patent is extended or adjusted under 35 U.S.C. 154(b) by 851 days.

(21) Appl. No.: 10/482,926

(22) PCT Filed: Jul. 4, 2002

(86) PCT No.: PCT/JP02/06771

§ 371 (c)(1),
(2), (4) Date: Jan. 6, 2004

(87) PCT Pub. No.: WO03/004641

PCT Pub. Date: Jan. 16, 2003

(65) Prior Publication Data

US 2004/0197858 A1    Oct. 7, 2004

(30) Foreign Application Priority Data

Jul. 6, 2001    (JP)    ............................. 2001-206919

(51) Int. Cl.
*C12P 21/04*    (2006.01)
(52) U.S. Cl. .................... 435/69.6; 435/69.1; 435/6; 536/23.1
(58) Field of Classification Search .............. 530/350, 530/300, 412, 413, 383; 435/69.1, 68.1, 435/69.6, 320.1, 212, 240.2; 514/44; 536/23.5
See application file for complete search history.

(56) References Cited

U.S. PATENT DOCUMENTS 5,693,499 A * 12/1997 Yonemura et al. .......... 435/69.6

FOREIGN PATENT DOCUMENTS

| JP | 3168087 | 7/1991 |
| WO | 9204378 A1 | 3/1992 |
| WO | 9600577 A1 | 1/1996 |
| WO | WO 96/41868 | 12/1996 |
| WO | WO 99/58699 | 11/1999 |
| WO | WO 01/04146 A2 | 1/2001 |

OTHER PUBLICATIONS

Seop So, In et al "Purification and Activation of Recombinant Human Prethrombin 2 Produced in *E. coli*" Korean Biochem. J. (1992) vol. 25, No. 1, pp. 60-65.
Russo, et al., "Stable expression and purification of a secreted human recombinant prethrombin-2 and its activation to thrombin", Protein Expression and Purification. 1997, vol. 10, No. 2, 214-225.
Nishida, et al., "cDNA cloning and deduced Amino acid sequence of prothrombin activator (ecarin) from Kenyan Echis carinatus venom", Biochemistry. 1995, vol. 34, No. 5, 1771-1779.

* cited by examiner

*Primary Examiner*—Hope A Robinson
(74) *Attorney, Agent, or Firm*—Browdy and Neimark, PLLC

(57) ABSTRACT

A genetic recombinant human thrombin is provided. Human thrombin is efficiently prepared by the genetic engineering technique comprising the steps: (1) culturing a transfectant animal cell transfected with an expression vector in which a gene encoding human prethrombin is incorporated to the downstream of a promoter so as to produce and accumulate prethrombin in culture supernatant and recovering the produced human prethrombin; (2) treating a solution containing human prethrombin recovered in step (1) with ecarin so as to convert human prethrombin into human thrombin; and (3) purifying the solution obtained after the above activation process to obtain purified human thrombin. The present invention allows for provision of human thrombin in a large scale in a safe and economical manner due to exclusion of blood-derived components.

7 Claims, 2 Drawing Sheets lane1; MW marker
lane2,6; Culture supernatant
lane3,7; After SP chromatography
lane4,8 After treatment with ecarin
lane5,9 After passing through hirudin column 1. MW marker
2. Active fraction of sulfate Cellulofine
3. Active fraction of gel filtration

SEQUENCE LISTING

<160> NUMBER OF SEQ ID NOS: 14

<210> SEQ ID NO 1
<211> LENGTH: 25
<212> TYPE: DNA
<213> ORGANISM: Artificial Sequence
<220> FEATURE:
<223> OTHER INFORMATION: Primer

<400> SEQUENCE: 1
aaaagcttgc catcatggtt cgacc                                    25

<210> SEQ ID NO 2
<211> LENGTH: 36
<212> TYPE: DNA
<213> ORGANISM: Artificial Sequence -continued

```
<220> FEATURE:
<223> OTHER INFORMATION: Primer

<400> SEQUENCE: 2
cggaggccaa ggcctgtctc cgttcttgcc aatccc                                36

<210> SEQ ID NO 3
<211> LENGTH: 36
<212> TYPE: DNA
<213> ORGANISM: Artificial Sequence
<220> FEATURE:
<223> OTHER INFORMATION: Primer

<400> SEQUENCE: 3
aacggagaca ggccttggcc tccgctcagg aacgag                                36

<210> SEQ ID NO 4
<211> LENGTH: 31
<212> TYPE: DNA
<213> ORGANISM: Artificial Sequence
<220> FEATURE:
<223> OTHER INFORMATION: Primer

<400> SEQUENCE: 4
ggggatcctg ttagtctttc ttctcgtaga c                                     31

<210> SEQ ID NO 5
<211> LENGTH: 30
<212> TYPE: DNA
<213> ORGANISM: Artificial Sequence
<220> FEATURE:
<223> OTHER INFORMATION: Primer

<400> SEQUENCE: 5
atggcgcacg tccgaggctt gcagctgcct                                       30

<210> SEQ ID NO 6
<211> LENGTH: 29
<212> TYPE: DNA
<213> ORGANISM: Artificial Sequence
<220> FEATURE:
<223> OTHER INFORMATION: Primer

<400> SEQUENCE: 6
ctactctcca aactgatcaa tgaccttct                                        29

<210> SEQ ID NO 7
<211> LENGTH: 29
<212> TYPE: DNA
<213> ORGANISM: Artificial Sequence
<220> FEATURE:
<223> OTHER INFORMATION: Primer

<400> SEQUENCE: 7
aagaattcgt cgacctactc tccaaactg                                        29

<210> SEQ ID NO 8
<211> LENGTH: 27
<212> TYPE: DNA
<213> ORGANISM: Artificial Sequence
<220> FEATURE:
<223> OTHER INFORMATION: Primer

<400> SEQUENCE: 8
tcttctcact ctctggagca gcgaccg                                          27
```

<210> SEQ ID NO 9
<211> LENGTH: 18
<212> TYPE: DNA
<213> ORGANISM: Artificial Sequence
<220> FEATURE:
<223> OTHER INFORMATION: Primer

<400> SEQUENCE: 9
accgccacaa gtgagtac                                                       18

<210> SEQ ID NO 10
<211> LENGTH: 34
<212> TYPE: DNA
<213> ORGANISM: Artificial Sequence
<220> FEATURE:
<223> OTHER INFORMATION: Primer

<400> SEQUENCE: 10
aagaattcgt cgaccaccat ggcgcacgtc cgag                                     34

<210> SEQ ID NO 11
<211> LENGTH: 1072
<212> TYPE: DNA
<213> ORGANISM: Homo sapiens

<400> SEQUENCE: 11
gaattcgtcg accaccatgg cgcacgtccg aggcttgcag ctgcctggct gcctggccct        60
ggctgccctg tgtagccttg tgcacagcca gcatgtgttc ctggctcctc agcaagcacg       120
gtcgctgctc cagagagtga agaaccgc cacaagtgag taccagactt tcttcaatcc         180
gaggaccttt ggctcgggag aggcagactg tgggctgcga cctctgttcg agaagaagtc       240
gctggaggac aaaaccgaaa gagagctcct ggaatcctac atcgacgggc gcattgtgga       300
gggctcggat gcagagatcg gcatgtcacc ttggcaggtg atgctttttcc ggaagagtcc      360
ccaggagctg ctgtgtgggg ccagcctcat cagtgaccgc tgggtcctca ccgccgccca       420
ctgcctcctg tacccgccct gggacaagaa cttcaccgag aatgaccttc tggtgcgcat       480
tggcaagcac tcccgcacca ggtacgagcg aaacattgaa aagatatcca tgttggaaaa       540
gatctacatc cacccccagg t acaactggcg ggagaacctg gacccgggaca ttgccctgat   600
gaagctgaag aagcctgttg ccttcagtga ctacattcac cctgtgtgtc tgcccgacag       660
ggagacggca gccagcttgc tccaggctgg atacaagggg cgggtgacag gctggggcaa       720
cctgaaggag acgtggacag ccaacgttgg taaggggcag cccagtgtcc tgcaggtggt       780
gaacttgccc attgtggagc ggccggtctg caaggactcc acccggatcc gcatcactga       840
caacatgttc tgtgctggtt acaagcctga tgaagggaaa cgaggggatg cctgtgaagg       900
tgacagtggg ggaccctttg tcatgaagag cccctttaac aaccgctggt atcaaatggg       960
catcgtctca tggggtgaag ctgtgaccgg ggatgggaaa tatggcttct acacacatgt      1020
gttccgcctg aagaagtgga tacagaaggt cattgatcag tttggagagt ag             1072

<210> SEQ ID NO 12
<211> LENGTH: 1863
<212> TYPE: DNA
<213> ORGANISM: Echis carinatus

<400> SEQUENCE: 12
ctcgagatga tccagattct cttggtaatt atatgcttag cagttttttcc atatcaaggt       60
tgctctataa tcctgggatc tgggaatgtt aatgattatg aagtagtgta ccacaaaaaa       120

-continued

```
gtcactgcat tgcccaaagg agcagttcag cagcctgagc aaaagtatga agatgccatg      180
caatatgaat ttgaagtgaa gggagagcca gtggtccttc acctagaaaa aaataaagaa      240
cttttttcag aagattacag tgagactcat tattcgtctg atgacagaga aattacaaca      300 aaccettcag ttgaggatca ctgctattat catggacgga tccagaatga tgctgagtca      360
actgcaagca tcagtgcatg caatggtttg aaaggacatt tcaagcttcg aggggagacg      420
tactttattg aaccettgaa gattcccgac agtgaagccc atgcagtcta caaatatgaa      480
aacatagaaa atgaggatga agcccccaaa atgtgtgggg taacccagga taattgggaa      540
tcagatgaac ccatcaaaaa gactttgggg ttaattgttc ctcctcatga acgaaaattt      600
gagaaaaaat tcattgagct tgtcgtagtt gtggaccaca gtatggtcac aaaatacaac      660
aatgattcaa ctgctataag aacatggata tatgaaatgc tcaacactgt aaatgagata      720
tacttacctt tcaatattcg tgtagcactg gttggcctag aattttggtg caatggagac      780
ttgattaacg tgacatccac agcagatgat actttgcact catttggaga atggagagca      840
tcagatttgc tgaatcgaaa aagacatgat catgctcagt tactcacgaa cgtgacactg      900
gatcattcca ctcttggaat cacgttcgta tatggcatgt gcaaatcaga tcgttctgta      960
gaacttattc tggattacag caacataact tttaatatgg catatataat agcccatgag     1020
atgggtcata gtctgggcat gttacatgac acaaaattct gtacttgtgg ggctaaacca     1080
tgcattatgt ttggcaaaga aagcattcca ccgcccaaag aattcagcag ttgtagttat     1140
gaccagtata acaagtatct tcttaaatat aacccaaaat gcattcttga tccacctttg     1200
agaaaagata ttgcttcacc tgcagtttgt ggaaatgaaa tttgggagga aggaagaa       1260 tgtgattgtg gttctcctgc agattgtcga aatccatgct gtgatgctgc aacatgtaaa     1320
ctgaaaccag gggcagaatg tggaaatgga gagtgttgtg acaagtgcaa gattaggaaa     1380
gcaggaacag aatgccggcc agcaagggat gactgtgatg tcgctgaaca ctgcactggc     1440
caatctgctg agtgtcccag aaatgagttc caaggaatgg acaaccatg ccttaacaac      1500 tcgggttatt gctacaatgg ggattgcccc atcatgttaa accatgtat tgctctcttt      1560 agtccaagtg caactgtggc tcaagattca tgttttcaga ggaacttgca aggcagttac     1620
tatggctact gcacaaagga aattggttac tatggtaaaa ggtttccatg tgcaccacaa     1680
gatgtaaaat gtggcagatt atactgctta gataattcat tcaaaaaaaa tatgcgttgc     1740
aagaacgact attcatacgc ggatgaaaat aagggaatga ttgaacctgg aacaaaatgt     1800
gaagatggaa aggtctgcat caacaggaag tgtgttgatg tgaatacagc ctactaactc     1860
gag                                                                  1863
```

<210> SEQ ID NO 13
<211> LENGTH: 13
<212> TYPE: PRT
<213> ORGANISM: Artificial Sequence
<220> FEATURE:
<223> OTHER INFORMATION: Hirudine peptide

<400> SEQUENCE: 13

Lys Gly Asp Phe Glu Glu Ile Pro Glu Glu Tyr Leu Glu
 1               5                  10

<210> SEQ ID NO 14
<211> LENGTH: 20
<212> TYPE: PRT
<213> ORGANISM: Echis carinatus

```
<400> SEQUENCE: 14

Lys Asn Asp Tyr Ser Tyr Ala Asp Glu Asn Lys Gly Ile Val Glu
 1               5                  10                  15

Pro Gly Thr Lys Cys
                20
```

PROCESS FOR PRODUCING HUMAN THROMBIN BY GENE MODIFICATION TECHNIQUE

CROSS-REFERENCE TO RELATED APPLICATIONS

This application is a 371 national stage application of PCT/JP02/06771, filed Jul. 4, 2002, which claims benefit to Japan 2001-206919, filed on Jul. 6, 2001.

TECHNICAL FIELD

The present invention belongs to the field of medical drugs and specifically relates to thrombin that can be used as a hemostatic. More specifically, the present invention relates to a genetic recombinant thrombin prepared by the genetic engineering technique and a process for preparing the same.

BACKGROUND ART

Thrombin is a trypsin-like serine protease having the activity essential to maintenance and development of life such as formation of hemostatic thrombus or curing of wound. Thrombin includes meizothrombin, α-thrombin, β-thrombin and γ-thrombin, among which α-thrombin is most important from the physiological point of view. Prothrombin, a precursor of thrombin, is biosynthetically produced in the hepatocytes in a vitamin K dependent manner and its blood level is in a range of 100 to 150 µg/ml. A vitamin K dependent coagulation factor has a Gla containing region (Gla domain) at the N-terminal and binds to a phospholipid via $Ca^{2+}$ ion. It is known that, upon binding of the Gla domain to $Ca^{2+}$ ion, a high dimensional overall structure of the protein is altered to thereby exert a key function as interacting with cofactors.

Prothrombin undergoes activation by FXa-FVa complex on the phospholipids of the cellular membrane wherein Arg320-Ile321 bonding in prothrombin is cleaved through restricted cleavage to form meizothrombin having the Gal domain and Kringle domain. Subsequently, Arg271-Thr272 bonding is cleaved through restricted cleavage to form α-thrombin, which is released from the cellular membrane and exhibits a variety of physiological activities by restrictedly cleaving a number of plasma proteins or various thrombin receptors on the cellular membrane. Alpha-thrombin is a two-chained molecule consisting of A chain and B chain. When B chain essential to the enzymatic activity undergoes autolysis, β-thrombin or γ-thrombin is produced to thereby lose an ability to activate fibrinogen or platelets.

Most of the formed thrombin participates locally in formation of larger thrombus by binding to fibrinous thrombus. Alpha-thrombin not only converts fibrinogen into fibrin but also activates FXIII to trigger cross-linkage of fibrin. Besides, α-thrombin may accelerate coagulation by activating FVIII and FV, a cofactor of FIX and FXa, respectively, to proceed coagulation. Thus, thrombin plays an important role in hemostasis and hence is a highly useful protein for use as a hemostatic.

On the other hand, thrombin changes its substrate specificity upon binding to thrombomodulin on the vascular endothelial cells to activate Protein C to promote anticoagulation. Thus, utilizing this enzymatic activity, thrombin is also useful as a process enzyme for preparing activated Protein C, an anticoagulant. Moreover, α-thrombin may potently coagulate and activate platelets and also exhibits a mitogenic activity. Alpha-thrombin, as displaying such a variety of physiological activities, has been used as a reagent in various fields of research and expected to still increase its utility in future.

With such functions and activities, thrombin has been widely used as a hemostatic, a process enzyme or a reagent for research. For example, for hemorrhage at the upper digestive tracts, thrombin derived from blood has been endoscopically spread or orally administered with successful hemostasis. Also, a fibrin paste used as a tissue adhesive comprises thrombin derived from blood together with fibrinogen and FXIII.

DISCLOSURE OF THE INVENTION

However, the thrombin materials described above are isolated from human or bovine blood and hence may also contain various dangerous factors derived from source blood that are considered to exert adverse effects on human. There is a fear that e.g. virus causing hepatitis such as HAV, HBV, HCV, HEV or TTV, virus causing immunodeficiency diseases such as HIV, or abnormal prion causing CJD etc. are present in the thrombin materials. In fact, drug damage caused by blood preparations contaminated with these dangerous factors has been a big social problem. Moreover, since human or bovine blood is derived from living material, there is no guarantee that it is stably provided. This is, in view of drugs, particularly an important and severe problem that must urgently be solved.

According to the conventional method, thrombin is prepared by activating prothrombin, a precursor of thrombin, with FXa derived from blood, i.e. blood-derived FXa is used for the activation process. Thus, even if a precursor of thrombin is prepared by the genetic engineering technique, as far as blood-derived FXa is used as the activating enzyme, a fear of contamination of blood components cannot be excluded. For preparing FXa by the genetic engineering technique, a precursor thereof, X, must be prepared by the genetic engineering technique and activated with FIXa. Further, for preparing FIXa by the genetic engineering technique, a precursor thereof, IX, must be prepared by the genetic engineering technique and activated with another coagulation factor. In this way, unless the most upstream enzyme in the cascade of coagulation reaction is prepared by the genetic engineering technique, thrombin cannot be prepared that is free from danger of contaminated blood components.

Taking into consideration a risk and limitation due to the use of blood as a source material for preparing thrombin and activating enzymes, alternative source and method allowing for provision of thrombin in a safer and more stable manner is desired. With this background, expression of thrombin has been reported using microorganism or animal cells as a host.

However, the conventional methods are disadvantageous in that, for example, thrombin expressed in *E. coli* forms aggregation, called inclusion body, which makes it difficult to recover thrombin. Specifically, to dissolve aggregation and to refold therefrom a functional protein is much inefficient and hence is not worthwhile to be applied to industrial usage (J. Biol. Chem. 270, 163-169, 1995). Also, an expression system with hamster culture cells has poor expression level and hence is not practical (Protein exp. purif., 10, 214-225, 1997). Moreover, in these methods, thrombin is expressed in a precursor form and therefore must be activated with the activating enzyme such as FXa, which however is not a recombinant enzyme and hence renders contamination of blood components not yet being excluded. Thus, in accordance with the conventional methods, it has been difficult to stably provide human thrombin with safety and at economical cost.

Under the circumstances, the present inventors have investigated to solve the problems described above and as a result succeeded in completing the present invention that provides a safe and economical process for preparing human thrombin. Specifically, the present inventors have constructed plasmids wherein either a gene encoding a human thrombin precursor or a gene encoding its activating enzyme is linked to the downstream of a potent promoter (i.e. beta-actin promoter), and incorporated said plasmids into animal cells to establish a high expression system for each of the genes incorporated, to thereby allow for providing thrombin and its activating enzyme in a large amount with safety, which the conventional method could not hitherto attain. In combination of thrombin and its activating enzyme thus produced, the present inventors have succeeded in providing active thrombin in a large amount with safety.

BEST MODE FOR CARRYING OUT THE INVENTION

Figure 1:
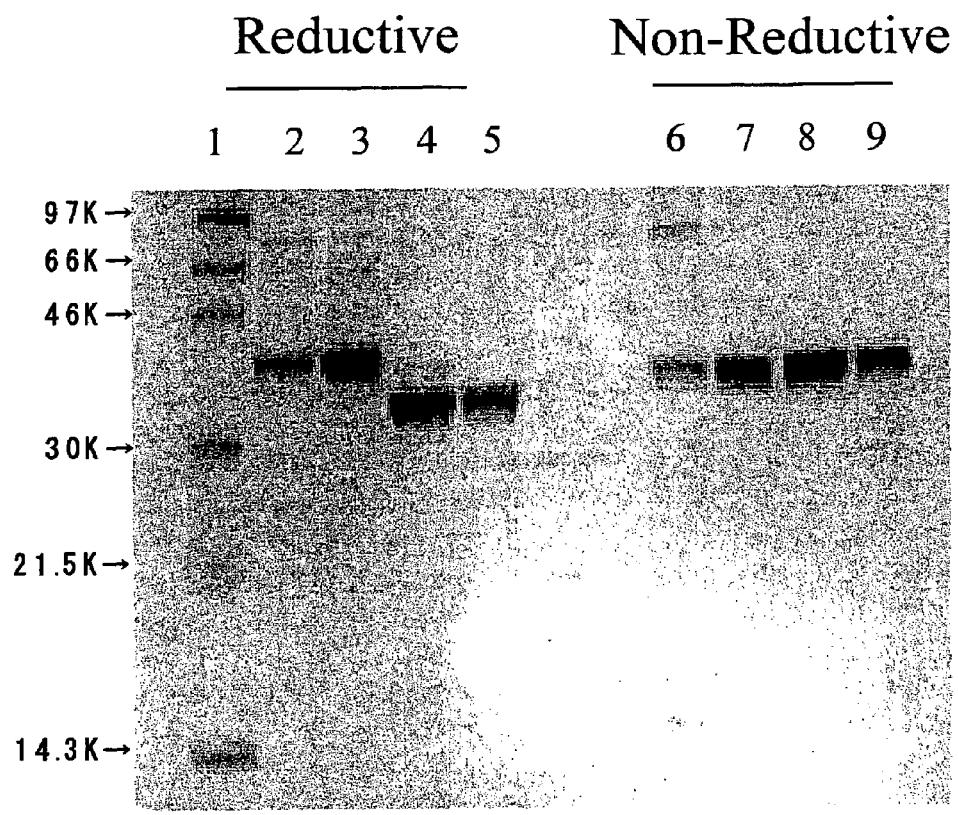
FIG. 1 shows the results of SDS-PAGE and protein staining for fractions obtained in each purification step of prethrombin-2 from culture supernatant of prethrombin-2-producing SP2/0.

As described above, prothrombin consists of Gla domain, Kringle domain and serine protease domain, among which Gla and Kringle domains undergo post-translational modification which may possibly be a rate-limiting process for protein production. On the other hand, α-thrombin consisting of A chain and B chain is a minimum active entity exerting the biological activity of thrombin. From these points of view, a gene encoding prethrombin-2 (hereinafter also referred to as "prethrombin"), which is a single-chained protein consisting of A-B chain, is selected for expression. It is expected that the use of a gene encoding prethrombin will result in more efficient transcription and translation than the use of a gene encoding prothrombin as a size of prethrombin mRNA is smaller than prothrombin mRNA.

Specifically, cDNAs were synthesized using mRNAs isolated from the human liver as a template and then a prothrombin gene was amplified by PCR using primers designed from the sequence of prothrombin gene. With the thus amplified prothrombin gene, a prethrombin-2 gene of interest was further amplified. Any high expression vector for animal cell host may be used without limitation but the most preferable embodiment includes a modified plasmid vector improved from chicken β-actin promoter-based expression plasmid pCAGG (Japanese patent publication No. 168087/1991) possessed by the present inventors, to which the amplified prethrombin gene is inserted to construct an expression plasmid. A leader sequence to be used in such a plasmid includes those derived from an innate thrombin gene or from other genes. As a consequence of transfection of the expression plasmid as constructed above into an animal cell, an animal cell could be obtained that exhibits such a high expression level as hitherto not being reported. An animal cell to be used as a host cell may include a cultured cell derived from hamster, mice, or human, preferably Chinese hamster ovary cell (CHO cell), mouse myeloma cell, BHK21 cell, 293 cell, COS cell, and the like.

Besides, in place of FXa, which has hitherto been used as an activating enzyme of thrombin, the present inventors used ecarin, an enzyme having the same activity as FXa, preferably recombinant ecarin, which could successfully be prepared by the high expression system of the present invention.

Ecarin is a snake venom-derived protease isolated from *Echis carinatus* (T. Morita et al.: J. Biochem. 83, 559-570, 1978), known to specifically activate prothrombin. A cDNA encoding ecarin has been cloned by S. Nishida et al. (Biochemistry, 34, 1771-1778, 1995) to reveal its structure. Ecarin, a glycoprotein, is a metalloprotease, a mature form of which has 426 amino acid residues in total, having a mosaic structure comprising a $Zn^{2+}$ chelate, a disintegrin domain and a Cys-rich domain, with 61% homology to an H chain of RVV-X (Russell's viper venom X activator). Ecarin is quite a distinct enzyme from Factor Xa since its enzymatic activity is inactivated by EDTA but is not inhibited by DFP or anti-thrombin III. In addition to ecarin, other activating enzymes with similar activity to FXa may also be utilized.

Ecarin exerts its thrombin-activating activity upon activation of an ecarin precursor by the action of protease such as trypsin or plasmin. Thus, for activation of thrombin, activation of an ecarin precursor with trypsin etc. is necessary. In accordance with the present invention, however, activation of an ecarin precursor may be done simultaneously in the purification process of a recombinant ecarin without using trypsin etc.

Specifically, like in the case of prethrombin, a gene encoding ecarin is amplified by PCR and incorporated into an expression vector derived from chicken β-actin promoter-based expression plasmid pCAGG to construct an expression vector. An animal cell in which the resulting plasmid was introduced could express a sufficient level of ecarin of interest. An animal cell to be used as a host cell may include a cultured cell derived from hamster, mice, or human like in the case of thrombin.

After purification from the obtained culture supernatant by ion exchange chromatography and gel filtration, ecarin could be isolated as an active protein without the use of an activating enzyme such as trypsin. In accordance with the devise of the present inventors, the ecarin protein expressed in an animal cell could simultaneously be purified and activated. The same effect and technique may be expected for other activating enzymes than ecarin if appropriately devised.

The thus obtained recombinant ecarin is used to activate the substrate recombinant prethrombin prepared above. The resulting recombinant α-thrombin may be purified to high purity by affinity chromatography with a hirudin peptide known to specifically react with thrombin, preferably by column chromatography with immobilized hirudin peptide. Thrombin may also be purified by any combination of various formats of chromatography.

When compared with natural α-thrombin derived from blood, the purified recombinant α-thrombin exhibited similar properties, suggesting that the recombinant α-thrombin prepared by the present inventors is a protein akin to naturally occurring α-thrombin.

As described above, the present inventors have successfully prepared activated human thrombin only by preparing both thrombin and ecarin protein precursors by the genetic engineering technique but without need of other enzymes.

The present invention is explained in more detail by means of the following Examples which are not intended to restrict a scope of the present invention in any sense. Reagents used in the following Preparation and Examples were obtained from Pharmacia, BioRad, Wako Pure Chemical Industries, Ltd., TAKARA SHUZO CO., Ltd., Toyobo, and New England BioLabs.

EXAMPLE 1

Construction of Expression Plasmid (1) Construction of Expression Plasmid pCAGG-S1 (Sal)

A chicken β-actin promoter-based expression plasmid pCAGG (Japanese Patent Publication No. 168087/1991) was digested with restriction enzyme EcoRI, blunt-ended with T4 DNA polymerase, and then ligated with T4 DNA ligase in the presence of phosphorylated XhoI linker to construct pCAGG (Xho). The obtained pCAGG(Xho) was digested with restriction enzyme SalI, blunt-ended with T4 DNA polymerase, and then ligated with T4 DNA ligase to construct pCAGG-Pv2. The resulting pCAGG-Pv2 was digested with restriction enzyme XhoI and then treated with S1 nuclease to erase several nucleotides in the vicinity of the XhoI recognition site. After the nuclease treatment, a single chain region was modified with T4 DNA polymerase in the presence of dNTPs and then ligated with T4 DNA ligase in the presence of phosphorylated SalI linker to construct pCAGG-S1 (Sal).

(2) Construction of Expression Plasmid pCAGG-S1 (Sal).dhfr

Expression plasmid pSV2-dhfr bearing DHFR gene (S. Subramani et al., Mol. Cell. Biol., 1, p.854-864, 1981) was digested with restriction enzyme BglII, blunt-ended with T4 DNA polymerase, and ligated with T4 DNA ligase to construct pSV2-dhfr-Bgn. The resulting pSV2-dhfr-Bgn was then digested with restriction enzyme PvuII and ligated with T4 DNA ligase in the presence of phosphorylated BglII linker to construct pSV2-dhfr-BgB. The obtained pSV2-dhfr-BgB was digested with restriction enzymes BglII and BamHI and was then subject to agarose gel electrophoresis to obtain a fragment of about 1.7 kbp. The expression plasmid pCAGG-S1 (Sal) obtained above was digested with restriction enzyme BamHI and then ligated to cyclize with the 1.7 kbp fragment to construct pCAGGS1 (Sal).dhfr.

(3) Construction of Expression Plasmid pCAGG-S1 (Sal).dhfr.neo

An aminoglycoside phosphotransferase (neo$^r$)-based expression plasmid pMC1neo-polyA (K. R. Thomas et al., Cell, 51, p.503-512, 1987) was digested with restriction enzyme XhoI and then ligated with T4 DNA ligase in the presence of a phosphorylated BamHI linker to construct pMC1neo-2B. The resulting pMC1neo-2B was digested with restriction enzyme BamHI and then subject to agarose gel electrophoresis to obtain a fragment of about 1.1 kbp. The expression plasmid pCAGG-S1 (Sal).dhfr obtained above was digested with restriction enzyme BamHI and then ligated to cyclize with the fragment of about 1.1 kbp to construct pCAGG-S1 (Sal).dhfr.neo.

(4) Construction of Modified DHFR-based Expression Plasmid pSV2-mdhfr

Expression plasmid pSV2-dhfr encoding DHFR cDNA was used as a template in PCR as described below. A first cycle of PCR was conducted with a combination of Primer 1 and Primer 2 and with a combination of Primer 3 and Primer 4. Nucleotide sequences of each primer are shown below:

```
Primer 1:
5'-AAAAGCTTGCCATCATGGTTCGACC          [SEQ ID NO: 1]

Primer 2:
5'-CGGAGGCCAAGGCCTGTCTCCGTTCTTGCCA    [SEQ ID NO: 2]
ATCCC
```

```
Primer 3:
5'-AACGGAGACAGGCCTTGGCCTCCGCTCAGGA    [SEQ ID NO: 3]
ACGAG

Primer 4:
5'-GGGGATCCTGTTAGTCTTTCTTCTCGTAGAC    [SEQ ID NO: 4]
```

With 5 ng template and each 100 pmol primers, amplification by Pyrobest DNA polymerase was carried out for 25 cycles. PCR was performed in accordance with the manufacturer's instruction of the enzyme. Amplified DNA fragments were purified on 1% agarose gel electrophoresis. Then, each about 20 ng of the DNA fragments amplified with a combination of Primer 1 and Primer 2 and with a combination of Primer 3 and Primer 4 were mixed together and PCR was performed with these DNA fragments as a template using Primer 1 and Primer 4. Nucleotide sequences of each primer are shown below. This PCR introduced a nucleic acid mutation that converts the 23rd leucine in DHFR into arginine. Amplified DNA fragments were digested with restriction enzymes HindIII-BamHI and then subject to 1% agarose gel electrophoresis to extract a DNA fragment of about 0.6 kbp. This DNA fragment was ligated to cyclize to a subcloning plasmid pUC19 previously digested with restriction enzymes HindIII-BamHI to construct pUC-mDHFR. A DNA sequence of this plasmid was determined to confirm that the desired mutation is accurately introduced and that there is no error in the other nucleotide sequences. The plasmid upon confirmation of its nucleotide sequence was again digested with restriction enzymes HindIII-BamHI and subject to agarose gel electrophoresis to extract a DNA fragment of about 0.6 kbp encoding DHFR gene with the introduced mutation. The expression plasmid pSV2-dhfr as described above was digested with restriction enzymes HindIII-BglII and then a DNA fragment of about 3 kbp was extracted from agarose gel electrophoresis. The resulting DNA fragment was ligated to cyclize to the DNA fragment encoding the mutant DHFR to construct pSV2-mdhfr.

(5) Construction of pCAGG-S1 (Sal).mdhfr

The expression plasmid pSV2-mdhfr was digested with restriction enzyme PvuII and ligated to cyclize with T4 DNA ligase in the presence of a phosphorylated BglII linker to construct pSV2-mdhfr-BgB. This plasmid was digested with restriction enzymes BglII-BamHI and a DNA fragment of about 1.7 kbp encoding mDHFR expression cassette was extracted from agarose gel electrophoresis. The expression plasmid pCAGGS1 (Sal) prepared in step (1) was digested with restriction enzyme BamHI and then ligated to cyclize with T4 DNA ligase to the 1.7 kbp fragment to construct pCAGG-S1 (Sal).mdhfr.

EXAMPLE 2

Preparation of Human Prethrombin-2 Gene

Using human liver mRNAs (manufactured by Sawaday-Technology) as a template, 1st strand cDNAs were synthesized by the method known in the art with Oligo dT as a primer using a reverse transcriptase (T-Primed First Strand Kit; manufactured by Amersham Pharmacia). Based on the cDNAs, primers as described below were designed and used for PCR. A primer of the sequence:
5'-ATGGCGCACGTCCGAGGCTTGCAGCTGCCT (PT1; SEQ ID NO: 5) for the gene corresponding to the N-terminal of prothrombin and a primer of the sequence:

5'-CTACTCTCCAAACTGATCAATGACCTTCT (PT2; SEQ ID NO: 6) for the gene corresponding to the C-terminal of prothrombin were used. PCR was performed with Pyrobest DNA polymerase in accordance with the manufacturer's instruction of this enzyme for 30 cycles for gene amplification. PCR described below was also performed in the similar manner.

Using the prothrombin cDNAs prepared above, a gene encoding prethrombin-2 was prepared. Primers as described below were synthesized and used for PCR with the prothrombin cDNAs as a template. Nucleotide sequences of each primer used are shown below:

```
Primer 1:
5'-AAGAATTCGTCGACCACCATGGCGCACGT    [SEQ ID NO: 7]
CCGAG

Primer 2:
5'-TCTTCTCACTCTCTGGAGCAGCGACCG      [SEQ ID NO: 8]

Primer 3:
5'-ACCGCCACAAGTGAGTAC               [SEQ ID NO: 9]

Primer 4:
5'-AAGAATTCGTCGACCTACTCTCCAAACTG    [SEQ ID NO: 10]
```

Primers 1 and 2 were used for amplification of a DNA encoding a preproleader region of prothrombin wherein a mutation was included to introduce Kozak consensus sequence into the initiation codon as well as to introduce upstream thereof recognition sites for restriction enzymes SalI and EcoRI. Primers 3 and 4 were used for amplification of a prethrombin-2 gene encoding a serine protease domain at the C-terminal of the prothrombin translation region wherein recognition sites for restriction enzymes SalI and EcoRI were introduced downstream of the termination codon. Primers 2 and 3 were treated with T4 polynucleotide kinase prior to PCR to phosphorylate their 5' terminus. PCR was performed with these primers to amplify the genes of interest. The amplified fragments were extracted from 1% agarose gel electrophoresis. Both DNAs encoding the preproleader region and the prothrombin-2 region were mixed together in a nearly equal amount and ligated to each other with T4 DNA ligase. Using the mixture as a template, PCR amplification was further carried out with Primer 1 and Primer 4. Among the amplified DNAs, a DNA of about 1.1 kbp was extracted from agarose gel electrophoresis to give a ligated product of the DNA sequence encoding preproleader and the DNA sequence encoding prethrombin-2. The N-terminal of this gene was digested with restriction enzyme EcoRI. A subcloning plasmid pTZ18R (Pharmacia) was digested with restriction enzymes SacI and PstI, blunt-ended with Mung bean nuclease, and ligated to cyclize with T4 DNA ligase to construct pTZΔScPt. The resulting plasmid pTZΔScPt was digested with restriction enzyme EcoRI and ligated to cyclize with the fragment encoding prethrombin with T4 DNA ligase to construct pTZ.PT. A DNA sequence of the resulting plasmid was determined by the method known in the art to confirm that a DNA encoding the preproleader region of prothrombin and a DNA encoding the prethrombin region are translated in the same frame. The prethrombin gene combined with the preproleader sequence is hereinafter referred to as "prethrombin structural gene" (SEQ ID NO: 11).

EXAMPLE 3

Construction of Human Prethrombin-2 Expression Plasmid

The prethrombin structural gene was incorporated into the plasmids pCAGG-S1 (SalI).dhfr.neo and pCAGG-S1 (SalI).mhfr as described in Example 1. The plasmids pCAGG-S1 (SalI).dhfr.neo and pCAGG-S1 (SalI).mdhfr were digested with restriction enzyme SalI and then dephosphorylated with bovine small intestine-derived alkaline phosphatase. The plasmid pTZ.PT obtained above was digested with restriction enzyme SalI and then a fragment of about 1.1 kbp encoding prethrombin-2 structural gene was purified by agarose gel electrophoresis. Then, the dephosphorylated plasmids and the fragment encoding prethrombin-2 structural gene were ligated to cyclize with T4 DNA ligase to construct pCAGG-S1.PT.dhfr.neo and pCAGG-S1.PT.mdhfr.

EXAMPLE 4

Expression of Human Prethrombin Using Animal Cells

The prethrombin expression plasmids as described in Example 3 were used to transform CHO DG44 (G. Urlaub et al., Somatic cell. Mol. Genet., 12, p.555-566 1986; hereinafter referred to as "CHO"cells and SP2/0 Ag14 (M. Shulman et al., Nature, 16, p.269-270, 1978; hereinafter referred to as "SP2/0"cells. The plasmid pCAGG-S1.PT.dhfr.neo was used for CHO cells whereas the plasmid pCAGG-S1.PT.mdhfr was used for SP2/0 cells. CHO cells were transfected by a modified calcium phosphate method (C. Chen et al., Mol. Cell. Biol., 7, p.2745-2752, 1987) whereas SP2/0 cells were transfected by Electroporation.

The expression plasmids for use in transfection were previously linearized by digestion with restriction enzyme PvuI.

Quantification of prethrombin was carried out by sandwich ELISA using anti-human thrombin antibody.

(1) Performance of Production for Prethrombin with CHO Cells

Using CHO cells, transfectants were selected from transfection as described below.

On the day previous to transfection, the cells were plated in MEM alpha medium with nucleic acids (manufactured by GIBCO-BRL) supplemented with 10% fetal calf serum (FCS; manufactured by GIBCO-BRL) in 10 cm dish at a cellular density of $5 \times 10^5$ cells/dish. After culture at 37° C. overnight, the cells were transfected with 20 μg/mL of the linearized expression plasmid pCAGG-S1.PT.dhfr.neo. After culture in 3% $CO_2$ incubator at 35° C. overnight, the cells were washed with Dulbecco PBS(−) and the culture medium was replaced with nucleic acid free MEMN alpha medium containing 10% dialyzed FCS and 500 μg/mL Geneticin (manufactured by GIBCO-BRL). For selection, culture was continued in 5% $CO_2$ incubator at 37° C. while replacing the culture medium every 3 to 4 days and emerged transfectants were pooled and assayed for their ability to produce prethrombin.

The transfected cells were plated in nucleic acid free MEM alpha medium supplemented with 10% dialyzed FCS at a density of $2 \times 10^5$ cells/mL and cultured overnight. The next day, the culture medium was replaced with serum free YMM medium (nucleic acid free MEM alpha medium with enriched amino acids/vitamins containing insulin, transferrin, ethanolamine and sodium selenite). After culture in 5% $CO_2$ incubator at 37° C. for 7 to 10 days, a prethrombin level in culture supernatant was measured. As a result, 20 µg/mL of prethrombin in the culture supernatant was detected. The cells were cultured with nucleic acid free MEM alpha medium containing 100 nmol/L methotrexate (MTX; manufactured by Wako Pure Chemical Industries, Ltd.), 10% dialyzed FCS and 500 µg/ml Geneticin for about 14 days while replacing the culture medium every 3 to 4 days. Thereafter, the cells were subject to dilution and passage culture and cultured for 14 days after replacing the culture medium with nucleic acid free MEM alpha medium containing 500 nmol/L MTX, 10% dialyzed FCS and 500 µg/mL Geneticin for gene amplification. The resulting cells were pooled and each 200 µL/well of the cells were inoculated onto 96 well plate at a concentration of 0.5 cell/well with the same culture medium for cloning by limiting dilution. Each of the obtained clones was assayed for an ability to produce prethrombin. Each clone was plated in nucleic acid free MEM alpha medium supplemented with 10% dialyzed FCS at a density of $2\times10^5$ cells/mL and cultured overnight. The next day, the culture medium was replaced with YMM medium. After culture in 5% $CO_2$ incubator at 37° C. for 7 to 10 days, a prethrombin level in culture supernatant was measured. Among the obtained clones, clone #10 expressed 90 µg/mL prethrombin-2 whereas clone #72 expressed 110 µg/mL prethrombin-2 in the culture supernatant.

(2) Performance of Production for Prethrombin with SP2/0 Cells

Using SP2/0 cells, transfectants were selected from transfection as described below.

SP2/0 cells were washed twice with cooled Dulbecco PBS (−) and $10^7$ cells suspended in 0.8 mL of PBS(−) were placed in a cuvette for Electroporation (electrode width 0.4 cm; manufactured by BIO-RAD). The linearized expression plasmid (40 µg) was added and mixed with pipette. One pulse was applied at 0.22 kv at 975 µF using Gene Pulser II (manufactured by BIO-RAD). After the cuvette was cooled on ice for 10 minutes, the cell suspension was diluted with MEM alpha medium with nucleic acids containing 10% fetal calf serum (FCS) to about 5,000 cells/50 µL, plated on five 96-well plates each at 50 µL/well, and cultured in 3% $CO_2$ incubator at 35° C. overnight. The next day, 50 µL/well of nucleic acid free MEM alpha medium containing 10% dialyzed FCS was added and culture was further continued overnight. The next day, 100 µL/well of nucleic acid free MEM alpha medium containing 10% dialyzed FCS and 100 nmol/L or 200 nmol/L MTX was added. After culture for 10 to 14 days, emerged transfectants at each well were assayed for their ability to produce prethrombin. The cells were plated with nucleic acid free MEM alpha medium containing 2% dialyzed FCS at a density of about $4\times10^5$ cells/mL. After culture for 24 hours, a prethrombin-2 level and a cell density in culture supernatant were measured to assay an ability to produce prethrombin per cell per hour. As a result, each of the transfectants was found to express 2 to 10 µg/day/$10^6$ cells of prethrombin.

Among these transfectants, those with the ability of high level production of prethrombin were selected and cultured with nucleic acid free MEM alpha medium containing 10% dialyzed FCS and 1 µmol/L MTX for about 14 days.

The obtained MTX resistant cells were adapted to serum free medium using YMM medium. YMM medium with 2% dialyzed FCS was used for culture and growth of the cells was confirmed. Thereafter, culture was continued while the serum level to be added was gradually lowered to 0.5% and further to 0.1%. After the cells were confirmed to proliferate well, they were cultured with completely serum free YMM medium. Growth of the cells was confirmed and then their ability to produce prethrombin was assayed by the method described above using YMM medium. Among the transfectants obtained, a clone #32 possessed an ability to produce 15 µg/day/$10^6$ cells prethrombin. The clone #32 cells were plated with YMM medium at a density of $3\times10^5$ cells/mL on a dish. After culture for about 7 days, a prethrombin level expressed in culture supernatant was measured. As a result, #32 expressed about 150 µg/mL prethrombin in culture supernatant.

EXAMPLE 5

Large Scale Culture of Prethrombin-producing Cells

The prethrombin-producing cells #32, adapted to serum free culture as described in Example 4, were subject to suspension culture with a spinner flask. After expansion of the cells, 250 mL of the cells were cultured with YMM medium in a 250 mL spinner flask (manufactured by Techne) at a density of $2\times10^5$ cells/mL. The cells were expanded to a 1 L spinner flask at a density of more than $1\times10^6$ cells/mL. After growth of the cells was confirmed, the cells were further expanded to five 1 L spinner flasks. The cells were cultured for about 7 days and then a prethrombin level in culture supernatant was measured to detect expression of about 100 µg/mL prethrombin-2.

EXAMPLE 6

Preparation of cDNA of Snake Venom Ecarin

Using the nucleotide sequence of ecarin cDNA reported in the literature (S. Nishida et al., Biochemistry, 34, p.1771-1778, 1995) as a template, PCR was conducted to introduce the recognition sites of restriction enzyme XhoI at both termini. The obtained gene was digested with restriction enzyme XhoI and subcloned into pUC18 to construct pUC.EC. A nucleotide sequence of the ecarin cDNA region of the resulting plasmid was determined by the conventional method to thereby obtain ecarin cDNA that has an exactly identical nucleotide sequence from the initiation codon to the termination codon to the sequence reported in the literature (SEQ ID NO: 12).

EXAMPLE 7

Construction of Ecarin Expression Plasmid

The ecarin cDNA was incorporated into the expression plasmid pCAGG-S1 (Sal).dhfr.neo as described in Example 1. The plasmid pCAGG-S1 (Sal).dhfr.neo was digested with restriction enzyme SalI and then dephosphorylated with bovine small intestine-derived alkaline phosphatase. The plasmid pUC.EC obtained above was digested with restriction enzyme XhoI and then a fragment of about 1.8 kbp encoding, ecarin cDNA was purified by agarose gel electrophoresis. Then, the dephosphorylated plasmid and the fragment encoding ecarin cDNA were ligated to cyclize with T4 DNA ligase to construct pCAGG-S1.EC.dhfr.neo.

EXAMPLE 8

Expression of Ecarin Using Animal Cells

The ecarin expression plasmid pCAGG-S1.EC.dhfr.neo described in Example 7 was used to transform CHO cells and SP2/0 cells. Quantification of ecarin was carried out on the basis of an activity to convert prothrombin into thrombin with commercially available snake venom derive ecarin (manufactured by Sigma) as a standard. An expression level was indicated as an activity unit (U/ML).

(1) Performance of Production for Ecarin with CHO Cells

Using CHO cells, transfectants were selected from transfection as described below.

On the day previous to transfection, the cells were plated in MEM alpha medium with nucleic acids supplemented with 10% fetal calf serum in 10 cm dish at a cellular density of $5 \times 10^5$ cells/dish. After culture at 37° C. overnight, the cells were transfected with 20 µg/mL of the linearized expression plasmid pCAGG-S1.EC.dhfr.neo. After culture in 3% $CO_2$ incubator at 35° C. overnight, the cells were washed with Dulbecco PBS(−) and the culture medium was replaced with nucleic acid free MEM alpha medium containing 10% dialyzed FCS and 500 µg/mL Geneticin. For selection, culture was continued in 5% $CO_2$ incubator at 37° C. while replacing the culture medium every 3 to 4 days and emerged transfectants were pooled and assayed for their ability to produce ecarin.

The transfected cells were plated in nucleic acid free MEM alpha medium supplemented with 10% dialyzed FCS at a density of $2 \times 10^5$ cells/mL and cultured overnight. The next day, the culture medium was replaced with serum free YMM medium. After culture in 5% $CO_2$ incubator at 35° C. for about 14 days, an ecarin level in culture supernatant was measured. As a result, 10 U/mL of ecarin in the culture supernatant was detected.

(2) Performance of Production for Ecarin with SP2/0 Cells

Using SP2/0 cells, transfectants were selected from transfection as described below.

SP2/0 cells were washed twice with cooled Dulbecco PBS (−) and $10^7$ cells suspended in 0.8 mL of PBS(−) were placed in a cuvette for Electroporation (electrode width 0.4 cm; manufactured by BIO-RAD). The linearized expression plasmid (40 µg) was added and mixed with pipette. One pulse was applied at 0.22 kv at 975 µF using Gene Pulser II (manufactured by BIO-RAD). After the cuvette was cooled on ice for 10 minutes, the cell suspension was diluted with MEM alpha medium with nucleic acids containing 10% fetal calf serum (FCS) to about 5,000 cells/50 µL, plated on five 96-well plates each at 50 µL/well, and cultured in 3% $CO_2$ incubator at 35° C. overnight. The next day, 50 µL/well of nucleic acid free MEM alpha medium containing 10% dialyzed FCS was added and culture was further continued overnight. The next day, 100 µL/well of nucleic acid free MEM alpha medium containing 1 mg/mL Geneticin and 10% dialyzed FCS was added. After culture for 10 to 14 days, emerged transfectants at each well were assayed for their ability to produce ecarin. The cells were plated with nucleic acid free MEM alpha medium containing 500 µg/mL Geneticin and 2% dialyzed FCS at a density of about $3 \times 10^5$ cells/mL. After culture for about 14 days, an ecarin level in culture supernatant was measured. As a result, each of the transfectants was found to express 2 to 10 U/mL of ecarin. Among these transfectants, each 200 µL/well of those producing a high level ecarin were plated on 96-well plate at a concentration of 0.5 cell/well with the same culture medium for cloning by limiting dilution. Each of the obtained clones was assayed for their ability to produce ecarin. Each clone was plated with nucleic acid free MEM alpha medium containing 2% dialyzed FCS at a density of $3 \times 10^5$ cells/mL. After culture in 5% $CO_2$ incubator at 35° C. for about 14 days, an ecarin level in culture supernatant was measured. Among the obtained clones, clone #1H-8 expressed 15 U/mL ecarin in culture supernatant.

This clone #1H-8 was adapted to serum free medium using YMM medium. YMM medium with 2% dialyzed FCS was used for culture and growth of the cells was confirmed. Thereafter, culture was continued while the serum level to be added was gradually lowered to 0.5% and further to 0.1%. After the cells were confirmed to proliferate well, they were cultured with completely serum free YMM medium. Growth of the cells was confirmed and then their ability to produce ecarin was assayed by the method described above using YMM medium. The clone #1H-8 after adaptation to serum free culture possessed an ability to produce 20 U/mL ecarin.

EXAMPLE 9

Large Scale Culture of Ecarin-producing Cells

The ecarin-producing cells #1H-8, adapted to serum free culture as described in Example 8, were subject to suspension culture with a spinner flask. After expansion of the cells, 250 mL of the cells were cultured with YMM medium in a 250 mL spinner flask (manufactured by Techne) at a density of $2 \times 10^5$ cells/mL. The cells were expanded to a 1 L spinner flask at a density of more than $1 \times 10^6$ cells/mL. After growth of the cells was confirmed, the cells were further expanded to five 1 L spinner flasks. The cells were cultured for about 7 days and then an ecarin level in culture supernatant was measured to detect expression of about 18 U/mL ecarin.

EXAMPLE 10

Preparation of Hirudin-immobilized Column

Hirudin is a thrombin-specific inhibitor isolated from leech. Based on the amino acid sequence of hirudin, a peptide of the sequence: Lys-Gly-Asp-Phe-Glu-Glu-Ile-Pro-Glu-Glu-Tyr-Leu-Glu as set forth in SEQ ID NO: 13 was synthesized with a peptide synthesizer (Applied). This peptide (10 mg) was coupled to formyl Cellulofine (1 ml; manufactured by Chisso Corporation) in accordance with the manufacturer's instruction.

EXAMPLE 11

Preparation of Antibody Against Partial Peptide of Ecarin

An amino acid sequence encoded by the ecarin cDNA was analyzed for its hydrophilic and hydrophobic regions in accordance with Hopp and Wood (T. P. Hopp et al., Proc. Natl. Acad. Sci. Vol. 78, 3824-3828, 1981). As a high hydrophilicity region, a peptide having the amino acid sequence: Lys-Asn-Asp-Tyr-Ser-Tyr-Ala-Asp-Glu-Asn-Lys-Gly-Ile-Val-Glu-Pro-Gly-Thr-Lys-Cys as set forth in SEQ ID NO: 14 was synthesized with a peptide synthesizer (manufactured by Applied). This peptide (500 µg) was inoculated to rabbit intradermally in the presence of Freund complete adjuvant on Day 0 and in the presence of Freund incomplete adjuvant on Day 14 and Day 28 to prepare a polyclonal antibody against the ecarin peptide. Western blot was used to confirm whether the obtained antibody recognizes ecarin. Natural ecarin was subject to SDS-PAGE in the absence of 2-mercaptoethanol. After electrophoresis, the gel was immersed in a transfer buffer (10 mM N-cyclohexyl-3-aminopropanesulfonic acid, 10% methanol, pH 11) for 5 minutes and then overlayed on PVDF membrane (Immovilon: Millipore) previously immersed in 100% methanol and the transfer buffer in this order to perform transfer at 160 mA for 16 hours using TRANS-BLOTCELL (BIO-RAD). After masking with TBST (50 mM Tris-HCl, pH 8.0; 150 mM NaCl; 0.05% Tween 20, containing 5% skim milk), the membrane was incubated with the serum diluted by 500-fold with TBST from rabbit to which the synthetic peptide was administered at room temperature for 1 hour and then washed with TBST. Then, the membrane was reacted with anti-rabbit IgG-HRP labeled antibody (Bio-Rad) diluted by 2,000-fold at room temperature for 1 hour. After washing, the membrane was dyed with Konica Immunostaining HRP 1000 (Konica) kit. As a result, the serum obtained by immunization with the synthetic peptide proved to specifically react with ecarin.

EXAMPLE 12

Purification of Recombinant Thrombin (1) Cation Exchange Chromatography

Culture supernatant (2000 ml) from the prethrombin-2-producing SP2/0 cells was adjusted to pH 6.0 with 1M citric acid and filtered through 0.45 µm filter to be used as a sample. The sample was applied to SP TOYOPEARL 550C (20 ml: Tosoh Corporation) column equilibrated with 20 mM citrate plus 0.05% PLURONIC F-68 (pH 6.0) buffer at a flow rate of 2 ml/min. The column was washed with the same buffer (100 ml) and then eluted with a gradient of salt concentration ranging from 50 mM to 1000 mM NaCl/20 mM citric acid (pH 6.0; 210 ml) at a flow rate of 2 ml/min. A portion of fractions was used for Western blot with the anti-thrombin antibody (Sigma) to identify fractions with eluted thrombin, which were pooled and dialyzed against 20 mM Tris-HCl (pH 8.5) buffer containing 0.1 M NaCl at 4° C. for 16 hours.

(2) Activation of Thrombin

After dialysis, to the pooled fraction (40 ml) of SP TOYO-PEARL 550C were added 25 ml of 1 M benzamidine and further the purified recombinant ecarin at a final concentration of 6.5 U/ml for reaction at 37° C. for 16 hours.

(3) Purification of Thrombin with Hirudin Peptide-immobilized Column

The reaction solution after ecarin treatment obtained in step (2) was applied to 10 ml of the gel immobilized with hirudin peptide prepared in Example 10 at 1 ml/min. After addition of the sample, the column was washed with 50 ml of 20 mM Tris-HCl (pH 8.5) buffer containing 0.5 M NaCl and then elution was performed with 50 ml of 20 mM Tris-HCl (pH 8.5) buffer containing 1 M potassium thiocyanate. These steps gave a highly purified α-thrombin with a final activity yield of 40%.

FIG. 1 shows the results of SDS-PAGE in the presence of 2-mercaptoethanol and protein staining with Coomassie Brilliant Blue dye for fractions obtained in each purification step.

EXAMPLE 13

Purification of Ecarin (1) Cation Exchange Chromatography

Culture supernatant (2000 ml) from the ecarin-producing SP2/0 cells was diluted with a twice amount of water, adjusted to pH 5.0 with 1M citric acid and filtered through 0.45 µm filter to be used as a sample. The sample was applied to Macro-Prep High S Support (20 ml: Bio-Rad Laboratories) column equilibrated with 20 mM citrate (pH 5.0) buffer at a flow rate of 4 ml/min. The column was washed with the same buffer (150 ml) and then eluted with a gradient of salt concentration ranging from 0 mM to 1000 mM NaCl/20 mM citric acid (pH 5.0; 210 ml) at a flow rate of 4 ml/min. A portion of fractions was used for Western blot with the anti-ecarin antibody obtained in Example 11 to identify fractions with eluted ecarin, which were pooled and dialyzed against 20 mM sodium hydrogen carbonate buffer (pH 9.0) containing 50 mM NaCl.

(2) Cation Exchange Chromatography

The dialyzed product obtained in the process of cation exchange chromatography (1) above was applied to sulfate Cellulofine (2 ml: SEIKAGAKU CORPORATION) column equilibrated with 20 mM sodium hydrogen carbonate buffer (pH 9.0) containing 50 mM NaCl at a flow rate of 0.5 ml/min. The column was washed with the buffer described above (14 ml) and then eluted with a gradient of salt concentration ranging from 50 mM to 600 mM NaCl/20 mM sodium hydrogen carbonate (pH 9.0; 20 ml) at a flow rate of 0.5 ml/min. A portion of fractions was used for Western blot with the anti-ecarin antibody obtained in Example 11 to identify and pool fractions with eluted ecarin.

(3) Gel Filtration

Figure 2:
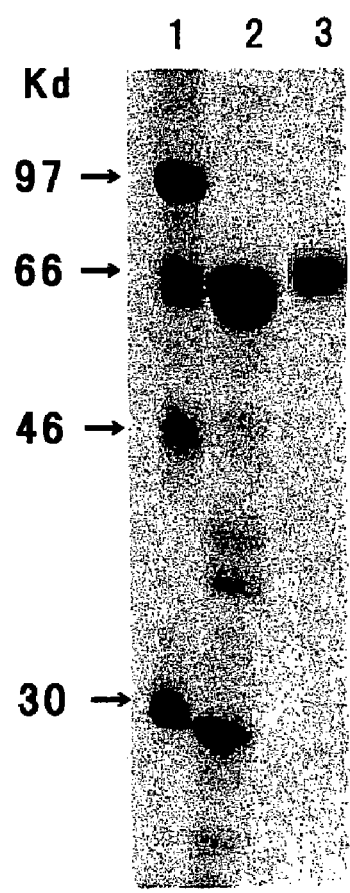
FIG. 2 shows the results of SDS-PAGE and protein staining for fractions obtained in gel filtration, the final step in ecarin purification from culture supernatant of ecarin-producing SP2/0.

The fractions containing the recombinant ecarin obtained in the process of chromatography (2) above were applied to gel filtration column HiLoad 16/60 (Pharmacia) equilibrated with 10 mM phosphate (pH 7.0) buffer containing 100 mM NaCl and fractionated at a flow rate of 0.5 ml/min. A marker for gel filtration (Bio Rad) was used as a molecular weight standard. Each of the fractions was measured for an ability to activate prothrombin to detect a peak activity in a fraction of about M.W. 80,000. The obtained fraction of purified ecarin was subject to SDS-PAGE in the presence of 2-mercaptoethanol with subsequent treatment with Coomassie Brilliant Blue. The obtained pattern is shown in FIG. 2.

The above three-step purification gave the recombinant ecarin with 13% of final activity yield and 12,000-fold higher specific activity as compared to culture supernatant.

EXAMPLE 14

Enzymatic Property of Recombinant α-thrombin

The purified recombinant α-thrombin prepared as described in Example 12 was determined for its enzymatic property, i.e. an activity to convert fibrinogen into fibrin, a dissociation constant for thrombomodulin, an activity to activate Protein C in the presence and absence of thrombomodulin, and an inhibition by antithrombin III. A purified α-thrombin derived from plasma (purchased from Hematologic Institute) was used as a positive control. As a result, the purified recombinant α-thrombin exhibited values in each of the enzymatic parameters that are equivalent to those of the purified plasma-derived α-thrombin as shown in Table 1.

TABLE 1

Comparison of enzymatic parameters between recombinant α-thrombin and blood-derived α-thrombin

|  | Recombinant α-thrombin | α-Thrombin from plasma |
|---|---|---|
| Activity to hydrolyze S-2238 | | |
| kcat (sec-1) | 160 ± 5 | 174 ± 19 |
| Km (μM) | 6.9 ± 1.5 | 8.3 ± 1.5 |
| kcat/Km (μ-1sec-1) | 23.3 ± 2.5 | 21.2 ± 2.7 |
| Conversion of fibrinogen into fibrin | | |
| kcat/Km (μM-1sec-1) for FpA | 10.9 ± 0.6 | 10.6 ± 0.8 |
| Dissociation constant for thrombomodulin | | |
| K dapp (nM) | 1.3 ± 0.1 | 1.4 ± 0.2 |
| Activation of Protein C (TM-) | | |
| kcat (min-1) | 9.1 ± 0.1 | 8.5 ± 0.2 |
| Km (μM) | 15.7 ± 0.3 | 16.3 ± 0.3 |
| kcat/Km (μM-1min-1) | 0.58 ± 0.01 | 0.52 ± 0.02 |
| Activation of Protein C (TM+) | | |
| kcat (min-1) | 86.6 ± 1.7 | 85.8 ± 3.5 |
| Km (μM) | 6.2 ± 0.5 | 5.5 ± 0.1 |
| kcat/Km (μM-1min-1) | 14.0 ± 1.5 | 15.5 ± 0.5 |
| Inhibition by ATIII | | |
| Secondary reaction constant (μM-1min-1) | 0.57 ± 0.01 | 0.65 ± 0.01 |

Measurement of activity of thrombin and ecarin in Examples as described above was performed as follows:

(1) Measurement of Thrombin Activity

An activity of thrombin was measured as described blow. A sample (20 μl), 50 mM Tris-HCl, pH 8.5 plus 50 mM NaCl buffer (60 μl), and 0.1% PLURONIC F-68 (20 μl) were added to 2008 tube (Falcon) and incubated at 37° C. for 3 minutes. A purified α-thrombin derived from human plasma (purchased from Hematologic Technology: HCT-0020) was used as a standard with dilution to 5, 2.5, 1.25, 0.625, and 0.3125 μg/ml using the same buffer. To the reaction mixture was added 100 μl of TestTeam developing substrate S-2238 (1 mM: DAIICH PURE CHEMICALS CO., LTD.) while stirring. After reaction at 37° C. for 5 minutes, the reaction was quenched with 800 μl of 0.1 M citric acid. The reaction solution (200 μl) was transferred to a 96-well plate and OD 405/650 was measured.

(2) Measurement of Ecarin Activity

An activity of ecarin was measured as described blow. A sample (20 μl), and 50 mM Tris-HCl, pH 8.5 plus 50 mM NaCl plus 0.1% PLURONIC F-68 buffer ("Buffer 1 "; 60 μl) were added to 2008 tube (Falcon). Thereto was added 0.01% trypsin (2 μl) and the mixture was stirred and incubated at 37° C. for 10 minutes. The sample was diluted with Buffer 1 as needed depending on its concentration. To the reaction solution was added 10 μl of prothrombin (0.4 mg/ml; purchased from Hematologic Technology) and the mixture was reacted at 37° C. for 5 minutes. Then, 10 mM EDTA (10 μl) and TestTeam developing substrate S-2238 (1 mM; 100 p1) were added to the reaction mixture while stirring. After reaction at 37° C. for 5 minutes, the reaction was quenched with 800 μl of 0.1 M citric acid. The reaction solution (200 μl) was transferred to a 96-well plate and OD 405/650 was measured. For quantification of an ecarin activity, ecarin derived from snake venom (commercially available from Sigma) was diluted to 25 mU/ml, 12.5, 6.25, and 3.125 mU/ml with Buffer 1. Each 20 μl of these standard solutions was used in place of the sample without addition of the trypsin solution and the steps described above following the addition of prothrombin were repeated.

With the conventional methods, an expression level of a recombinant thrombin has hitherto been reported as being about 25 μg/ml. By marked contrast, the expression system of thrombin constructed in accordance with the present invention allows for expression level of thrombin as high as about 150 μg/ml, which much exceeds the expression level attained by the conventional methods. Moreover, the present inventors have successfully prepared a recombinant ecarin for use as an activating enzyme, thus establishing a method for preparing human thrombin with complete safety by excluding components derived from blood. Thus, the present invention allows for provision of human thrombin in a large scale in a safe and economical manner due to exclusion of blood-derived components to thereby highly contribute to the field of medical treatment and research.

The invention claimed is:

1. A process for preparing human α-thrombin by a genetic engineering technique which comprises the following steps:
   (1) culturing a transfectant animal cell transfected with an expression vector in which a DNA encoding human prethrombin-2 with an upstream prothrombin preproleader sequence is incorporated to the downstream of a chicken β-actin promoter so as to produce and accumulate human prethrombin-2 at a high expression level of at least 90 µ/ml in culture supernatant and recovering the produced human prethrombin-2, wherein said DNA encoding human prethrombin-2 with an upstream preproleader sequence has the nucleotide sequence as set forth in SEQ ID NO:11;
   (2) treating a solution containing human prethrombin recovered in step (1) with ecarin so as to convert human prethrombin into human α-thrombin in a solution; and
   (3) purifying the solution obtained after the treatment in step (2) to obtain purified human α-thrombin.

2. The process for preparing the human α-thrombin of claim 1, wherein said expression vector further contains an amplification sequence and the transfectant is cultured under conditions suitable for DNA amplification.

3. The process for preparing the human α-thrombin of claim 2, wherein said amplification sequence is a DNA encoding dihydrofolate reductase.

4. The process for preparing the human α-thrombin of claim 1, wherein said transfectant is an animal cell selected from the group consisting of Chinese hamster ovary cell (CHO cell), mouse myeloma cell, BHK21 cell, 293 cell and COS cell.

5. The process for preparing the human α-thrombin of claim 1, wherein said ecarin used to convert human prethrombin-2 is prepared by a genetic engineering technique.

6. The process for preparing the human α-thrombin of claim 1, wherein said purifying of human α-thrombin consists of affinity chromatography with hirudin peptide.

7. The process for preparing the human α-thrombin of claim 1, wherein said transfectant is an animal cell selected from the group consisting of Chinese hamster ovary cell (CHO cell), mouse myeloma cell, BHK21 cell, 293 cell and COS cell.

* * * * *

UNITED STATES PATENT AND TRADEMARK OFFICE
CERTIFICATE OF CORRECTION

PATENT NO. : 7,635,577 B2 Page 1 of 1
APPLICATION NO. : 10/482926
DATED : December 22, 2009
INVENTOR(S) : Yonemura et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 946 days.

Signed and Sealed this

Ninth Day of November, 2010

David J. Kappos
*Director of the United States Patent and Trademark Office*